US000001160H

United States Statutory Invention Registration [19]

[11] Reg. Number: H1160

Maulding et al. [43] Published: Apr. 6, 1993

[54] IONTOPHORETIC DELIVERY OF PEPTIDES

[76] Inventors: Hawkins V. Maulding, Corey La., Mendham, N.J. 07945; James R. Siverly, 9 Henry St., Morristown, N.J. 07960

[21] Appl. No.: 617,824

[22] Filed: Nov. 26, 1990

[51] Int. Cl.[5] ..... A61M 1/30

[52] U.S. Cl. ..... 604/20; 204/299 R; 128/639

[58] Field of Search ..... 204/299 R; 604/20; 128/639, 803

[56] References Cited

U.S. PATENT DOCUMENTS

| | | | |
|---|---|---|---|
| 4,640,689 | 2/1987 | Sibalis | 604/20 |
| 4,702,732 | 10/1987 | Powers | 128/639 |
| 4,708,716 | 11/1987 | Sibalis | 604/20 |
| 4,786,277 | 1/1988 | Powers | 128/639 |
| 4,842,577 | 6/1989 | Konno | 128/803 |
| 4,919,648 | 4/1990 | Sibalis | 604/20 |
| 4,921,475 | 5/1990 | Sibalis | 604/20 |
| 4,942,883 | 8/1990 | Newman | 604/20 |

*Primary Examiner*—Richard D. Lovering
*Assistant Examiner*—Joseph D. Anthony

[57] ABSTRACT

The invention concerns a new system and method for iontophoretically delivering a polypeptide transdermally into animal tissue.

8 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

IONTOPHORSIS OF CALCITONIN IN MINIPIGS

■ – Iontophoresis at 200 μA/cm² and
—●— passive application. Patch area = 10 cm²; containing 3–4 milliliters of 12.5 mg/ml Calcitonin in 4% HPMC

IONTOPHORSIS OF CALCITONIN IN MINIPIGS

■ – Iontophoresis at 200 $\mu A/cm^2$ and
—●— passive application. Patch area = 10 $cm^2$; containing 3–4 milliliters of 12.5 mg/ml Calcitonin in 4% HPMC

IONTOPHORETIC DELIVERY OF PEPTIDES

BACKGROUND OF THE INVENTION

This invention relates to a manner of delivering substances into a mammalian body, and more particulary concerns delivery of polypeptide into a mammalian body.

Ionic substances have previously been delivered into body tissue by iontophoretic means. This method for delivering substances such as chemicals or drugs normally utilizes direct electrical current in contact with the skin, and drives these substances through intact skin to the interior of the animal body, including the blood stream. Iontophoresis has been shown to be useful in various medical applications and substances such a lidocaine, hydrocortisone and many other drugs have been so administered.

Various iontophoretic devices and systems have been previously described and comprise a source for generating current, a pair of electrodes and the ionic substance to be introduced into the body. The active electrode, the donor electrode that drives the desired substance through the skin, is of the same charge as the substance.

It is preferable that the active electrode also physically embrace a source for the drugs, and this can be accomplished by retaining the drug in a compatible matrix, such as a polymeric matrix, e.g. a gel or a solution contained by a semipermable membrane, or even a moist cloth or gauze and water system which will permit flow of electrically charged substance to and through the skin. Transdermal patches which contain the drug, a matrix and water are the preferred mode for transdermally administering the active agent to the human or non-human animal patient.

European Patent Application 0278 473 discloses a chemical composition and system for iontophoretic transport which comprises a protein, a cosolvent with negative Setschenow constant and water. The protein which may be used includes, but is not limited to, polypeptides having more than about 20 peptide units. The various proteins mentioned include but are not limited to calcitonin and insulin.

Iontophoretic transdermal delivery of insulin, which is a 51 peptide protein is disclosed by Chien, et al, J. Pharmaceutical Sciences 78, 5, 376–383 May 1989.

It is an object of the present invention to provide a means for iontophoretically delivering transdermally calcitonin, especially salmon calcitonin, into animal tissue.

It is a further object to provide a method for delivering calcitonin by iontophoretic transdermal means to a human or a non-human patient without the use of a cosolvent in the drug reservoir.

A further object is the provision of a transdermal device for delivering calcitonin by iontophoresis into animal tissue.

SUMMARY OF THE INVENTION

The invention is a new system and method for iontophoretically delivering a polypeptide, such as calcitonin, transdermally into animal tissue.

DESCRIPTION OF THE INVENTION

It has now been surprisingly found that a calcitonin, such as salmon calcitonin, which is a 32 amino acid polypeptide having a positive charge, may be iontophoretically introduced transdermally into mammalian tissue by means of continuous application of a voltage difference less than about ten volts with a simple aqueous electrode system. No need for cosolvent is required. Instead, a quantity of a calcitonin in a matrix consisting essentially of water may be driven through the epidermal layer into the blood stream. This avoids the undesirable complication of also transporting a cosolvent into the transdermal layer or into the blood stream of the human or non-human animal being administered the calcitonin.

The levels of calcitonin in the animal blood stream achieved by this method are therapeutic, this being accomplished in short periods of time and without injury or irritation to the epidermal layers.

Generally the matrix containing the calcitonin is in the form of an adhesive patch filled with a gel or polymeric substance capable of retaining the water and the calcitonin. A pH of 4–9 is acceptable, preferably a pH of 4.5–6, most preferably 4.5–5.5. The gel may consist of aqueous hydroxypropyl methylcellulose or other neutral gel forming polymers in water.

The electrical components of the electrodes usable are also known in the art and preferably are silver/silver chloride electrodes.

A convenient configuration for the reservoir containing the calcitonin would a two membrance system whereby the calcitonin, such as salmon calcitonin, in the gel and water matrix would be retained between the two membranes. A two chamber compartment on an adhesive patch, is a preferred embodiment of the iontophoretic system of this invention.

It should also be understood that it is preferred that no other ions of like charge to the drug be present in the transdermal patch. Preservative to prevent microbiological contamination is also useful. To avoid driving this preservative into the tissue, it is also understood that it should be neutral or negatively charged.

A current density from about 10 microamps ($\mu$A) per $cm^2$ about 300 $\mu A/cm^2$ may be used, higher currents being possible but increasing the chances of damage to the tissued involved. The preferrered current density is about 100–250 $\mu A/cm^2$.

EXAMPLE 1

Figure 1:
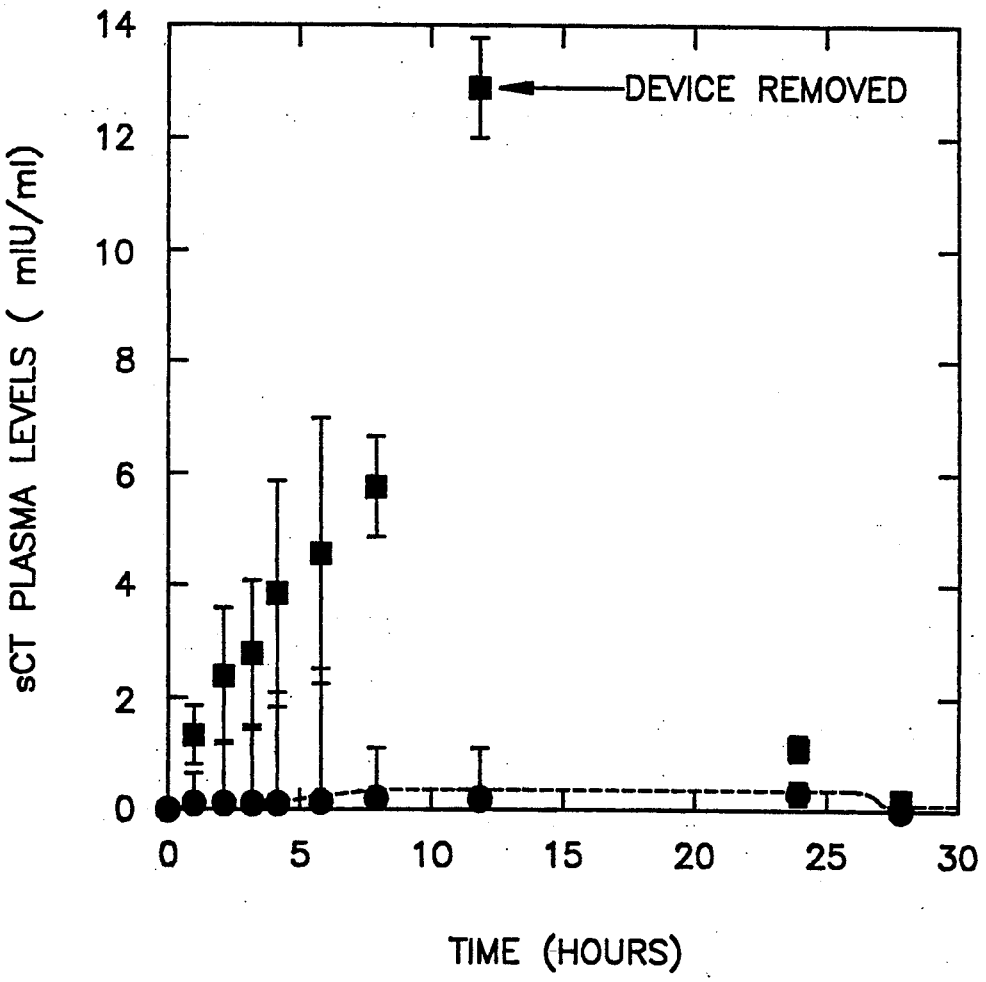
FIG. 1 shows the mean plasma levels of salmon calcitonin with respect to time in the test animals.

An iontophoretic device consisting of two patches, one containing a donor gel and a silver wire mesh electrode and the other a return electrode, and a constant current source is used. A tared donor compartment is filled with about 4 ml of 4% hydroxypropyl methylcellulose (Shin-Etsu, Tokyo, Japan) gel containing 12.5 mg of salmon calcitonin/g of gel. The weight of the filled patch is measured to calculate the amount of calcitonin added. The donor compartment is separated from the silver electrode by an anion selective membrane (Raipore #5030H) and the top chamber contains Signa Gel (Parker Labs, West Orange, N.J.). See Sanderson et al, J. Pharm. Sci. 76,215 (1987) and Parsi U.S. Pat. No. 4,731,049 respecting anion selective membranes. The donor gel is contained inside the patch by adhering a Spectra/Por 2 dialysis membrane (molecular weight cut off 12,000 to 14,000 Daltons; Spectrum, Los Angeles, Calif.) to the bottom of the patch. The return patch consists of a silver wire mesh electrode plated with chloride and a chamber filled with Signa Gel. The surface area of each patch exposed to the skin is 10 square cm.

EXAMPLE 2

The patches of Example 1 are applied to each of three male miniature swine both by iontophoresis and passively in a crossover fashion. In the first part of the study, two animals receive current while the other is a passive control. For the second phase of the study, animals receive the opposite treatment; see Table I below. The total current applied is 2mA or the equivalent of 200 μA/cm2. The patches are applied for 12 hours. After that time the current is stopped and all devices are removed. The gel remaining on the skin is recovered for analysis of residual salmon calcitonin not delivered. The amount remaining in the patch is determined by removing the excess gel from the patch, soaking the patch and dissolving the excess gel in pH 5 sodium acetate buffer.

Zero time blood samples are drawn the afternoon of the day before the devices are applied. Two ml of plasma from each animal is reserved for the zero sample and the rest pooled for use in the analysis.

Blood samples are drawn at 1,2,3,4,6,8,12,24,28,32,48 and 72 hours. For each sample the animal is turned on its back. At least 2 ml of blood is drawn from the vena cava into plastic syringes using an 18 gauge, 1.5 inch needle. The blood sample is transferred into chilled plastic tubes containing lithium heparin. The tubes are centriguged at 4° C. at 3,000 rpm for 10 minutes to isolate the plasma. The plasma is drawn off using a pipette and transferred to a plastic tube labeled with the number of the animal and the sample time. The plasma is stored frozen at −70° C. until all samples are collected. The concentration of calcitonin in each sample is determined by radioimmunoassay.

Results

The concentration of salmon calcitonin in the plasma for the two treatments is presented in Tables II and III. The mean plasma levels of the three animals at each sample time are plotted with respect to time in FIG. 1. Animal #149-5 aside, there was on average from 20 to 1000 times greater calcitonin concentrations with iontophoresis than with no current.

TABLE I

EXPERIMENTAL DESIGN

| Animal # | Part I | Part II |
|---|---|---|
| 149-1 | Iontophoresis | Passive |
| 149-4 | Iontophoresis | Passive |
| 149-5 | Passive | Iontophoresis |

TABLE II

SALMON CALCITONIN PLASMA LEVELS FOLLOWING IONTOPHORESIS (mIU/ml)

| | Pig Number | | | | |
|---|---|---|---|---|---|
| Time | 149-1 | 149-4 | 149-5 | Mean | SEM |
| 0 | 0.000 | 0.000 | 0.000 | 0.000 | 0.000 |
| 1 | 2.210 | 1.466 | 0.372 | 1.349 | 0.534 |
| 2 | 3.139 | 4.057 | 0.099 | 2.432 | 1.196 |
| 3 | 3.070 | 4.840 | 0.222 | 2.711 | 1.345 |
| 4 | 6.955 | 4.582 | 0.022 | 3.853 | 2.034 |
| 6 | 7.825 | 5.890 | 0.000 | 4.572 | 2.353 |

TABLE II-continued

SALMON CALCITONIN PLASMA LEVELS FOLLOWING IONTOPHORESIS (mIU/ml)

| | Pig Number | | | | |
|---|---|---|---|---|---|
| Time | 149-1 | 149-4 | 149-5 | Mean | SEM |
| 8 | 8.627 | 8.542 | 0.000 | 5.723 | 2.862 |
| 12 | 13.160 | 13.940 | 11.070 | 12.723 | 0.857 |
| 24 | 1.527 | 1.368 | 0.733 | 1.209 | 0.243 |
| 28 | 0.295 | 0.302 | 0.092 | 0.230 | 0.069 |
| 32 | 0.258 | 0.404 | 0.168 | 0.277 | 0.069 |
| 48 | 0.289 | 0.149 | 0.107 | 0.182 | 0.055 |
| 72 | 0.149 | 0.169 | 0.060 | 0.126 | 0.034 |

TABLE III

SALMON CALCITONIN LEVELS FOLLOWING PASSIVE ADMINISTRATION (mIU/ml)

| | Pig Number | | | | |
|---|---|---|---|---|---|
| Time | 149-1 | 149-4 | 149-5 | Mean | SEM |
| 0 | 0 | 0 | 0 | 0 | 0 |
| 1 | 0.020 | 0.086 | 0.031 | 0.045 | 0.020 |
| 2 | 0 | 0.115 | 0.182 | 0.099 | 0.053 |
| 3 | 0.027 | 0.055 | 0.261 | 0.114 | 0.073 |
| 4 | 0 | 0 | 0.295 | 0.098 | 0.098 |
| 6 | 0.064 | 0.032 | 0.431 | 0.175 | 0.128 |
| 8 | 0.061 | 0.077 | 0.579 | 0.239 | 0.170 |
| 12 | 0 | 0.035 | 0.510 | 0.181 | 0.164 |
| 24 | 0.111 | 0.695 | 0.075 | 0.293 | 0.200 |
| 28 | 0 | 0.089 | 0.084 | 0.090 | 0.004 |
| 32 | 0 | 0.068 | 0.103 | 0.057 | 0.030 |
| 48 | 0.032 | 0.058 | 0.065 | 0.051 | 0.010 |
| 72 | 0 | 0.053 | 0 | 0.017 | 0.017 |

The amount of calcitonin placed in each patch, the residual calcitonin recovered from the patch and the estimate of the amount of calcitonin transported, calculated from the difference between the amount applied and the amount recovered, are shown in Table IV.

TABLE IV

SALMON CALCITONIN DELIVERED

| Iontophoresis | 149-1 | 149-4 | 149-5 |
|---|---|---|---|
| Mg Applied | 38.4 | 43.7 | 39.1 |
| Mg Recovered | 12.4 | 30.8 | 35.3 |
| Mg Delivered | 26.0 | 12.9 | 3.8 |

We claim:

1. A device for transdermal transport of a chemical into animal tissue by electrolytic means comprising a calcitonin and water in a reservoir usable for iontophoretic administration.

2. A transdermal patch for delivering a calcitonin into the blood stream of a patient having in an electrode thereof a solution consisting essentially of a calcitonin and water.

3. A transdermal patch according to claim 2 wherein said calcitonin is salmon calcitonin.

4. A transdermal patch according to claim 3 wherein the solution additionally contains a preservative.

5. A method for transdermally transporting a calcitonin into animal tissue which comprises use of a device according to claims 1 or 2.

6. A method according to claim 5 wherein the solution additionally contains a neutral or anionic preservative.

7. A method for transporting salmon calcitonin into the blood stream of a patient which comprises using an iontophoretic patch containing in a donor electrode a solution of salmon calcitonin and water.

8. A method according to claim 7 wherein the donor electrode solution consists essentially of salmon calcitonin and water.

* * * * *